(12) United States Patent
Wakita

(10) Patent No.: US 11,801,010 B2
(45) Date of Patent: Oct. 31, 2023

(54) WALKING SENSE PRESENTATION DEVICE AND PRESENTATION METHOD

(71) Applicant: Wataru Wakita, Hiroshima (JP)

(72) Inventor: Wataru Wakita, Hiroshima (JP)

( * ) Notice: Subject to any disclaimer, the term of this patent is extended or adjusted under 35 U.S.C. 154(b) by 361 days.

(21) Appl. No.: 16/489,272

(22) PCT Filed: Feb. 27, 2018

(86) PCT No.: PCT/JP2018/007279
§ 371 (c)(1),
(2) Date: Aug. 27, 2019

(87) PCT Pub. No.: WO2018/159614
PCT Pub. Date: Sep. 7, 2018

(65) Prior Publication Data
US 2020/0060610 A1    Feb. 27, 2020

(30) Foreign Application Priority Data

Mar. 2, 2017 (JP) .................. 2017-038857

(51) Int. Cl.
*A61B 5/00* (2006.01)
*A61B 5/11* (2006.01)
(Continued)

(52) U.S. Cl.
CPC ............. *A61B 5/486* (2013.01); *A61B 5/112* (2013.01); *A61B 5/1116* (2013.01);
(Continued)

(58) Field of Classification Search
CPC ....... A61B 5/112; A61B 5/702; A61B 5/1121; A61B 5/1116; A63B 2071/0638; A63B 2230/62; A63B 2220/51
See application file for complete search history.

(56) References Cited

U.S. PATENT DOCUMENTS

2010/0271051 A1    10/2010    Sankai et al.
2011/0218466 A1    9/2011    Takahashi et al.
2015/0088408 A1    3/2015    Yamaoka

FOREIGN PATENT DOCUMENTS

CN    102245150 A    11/2011
CN    102670217 A  *  9/2012
(Continued)

OTHER PUBLICATIONS

English translation of CN 102670217 (Year: 2012).*
(Continued)

*Primary Examiner* — Alex M Valvis
*Assistant Examiner* — Yasmeen S Warsi
(74) *Attorney, Agent, or Firm* — K&L Gates LLP; Louis C. Cullman; Giorgios N. Kefallinos

(57) ABSTRACT

A femoral region supporter (2) supports a femoral region of a user (1) in a travel direction. A force detector (3) detects force received by the femoral region supporter (2) from the femoral region of the user (1). A walking motion estimator (4) estimates walking motion of the user (1) based on the force detected by the force detector (3). The video generator (5) generates a video to be presented to the user (1) based on the walking motion estimated by the walking motion estimator (4). The video presenter (6) presents the video generated by the video generator (5) to the user (1).

4 Claims, 19 Drawing Sheets

(51) Int. Cl.
*A63B 71/06* (2006.01)
*G06F 3/14* (2006.01)

(52) U.S. Cl.
CPC ............ *A61B 5/1121* (2013.01); *A61B 5/702* (2013.01); *A61B 5/7445* (2013.01); *A63B 71/0622* (2013.01); *G06F 3/14* (2013.01); *A63B 2071/0638* (2013.01); *A63B 2071/0666* (2013.01); *A63B 2220/16* (2013.01); *A63B 2220/51* (2013.01); *A63B 2230/62* (2013.01)

(56) References Cited

FOREIGN PATENT DOCUMENTS

| | | |
|---|---|---|
| CN | 104515521 A | 4/2015 |
| JP | 2000-516829 A | 12/2000 |
| JP | 2001-061992 A | 3/2001 |
| JP | 3200592 B | 8/2001 |
| JP | 2001-296951 A | 10/2001 |
| JP | 3373460 B | 2/2003 |
| JP | 3464976 B | 11/2003 |
| JP | 3550087 B | 8/2004 |
| JP | 2006-239086 A | 9/2006 |
| JP | 2006-345990 A | 12/2006 |
| JP | 2008-220580 A | 9/2008 |
| JP | 4269646 B | 5/2009 |
| JP | 2009-125506 A | 6/2009 |
| JP | 4313633 B | 8/2009 |
| JP | 2010-017390 A | 1/2010 |
| JP | 2014-195506 A | 10/2014 |
| JP | 2014-195510 A | 10/2014 |
| JP | 2016-168666 A | 9/2016 |
| WO | 2018/159614 A1 | 9/2018 |

OTHER PUBLICATIONS

Yamamoto et al., "A high immersive infinity walking system with HMD and load balance." Sep. 14, 2016, 11A-01, (The 21st Annual Conference of the Virtual Reality Society of Japan [USB]), non-official translation.

Yamamoto et al., A proposal low-cost infinity walking system with life-sized VR environment for appreciation of large cultural resource, non-official translation. Research report of Information Processing Society of Japan: Digital contents creation (DCC)), 2016-DCC-014 [online], Nov. 2, 2016, vol. 2016-DCC-14, No. 15, pp. 1-4.

Ohshima et al., Virtual-ISU: A locomotion interface for immersive VR gaming in seating position (3). 2016 Information Processing Society of Japan, 2016 [online], Nov. 5, 2016, pp. 295-300.

Cao et al., Walk-in-place locomotion interface with stepping forward, backward, jump and turning functions. Transactions of the Virtual Reality Society of Japan, Mar. 31, 2010, vol. 15, No. 1, pp. 53-62.

Takahashi et al., "Circular position sensor for locomotion interface." Proceedings of 15th conference of the Virtual Reality Society of Japan Annual Conference (CD-ROM), Sep. 15, 2010, pp. 408-411, non-official translation.

Noma, "VR Interface for Locomotive Sensation." Journal of the Society of Instrument and Control Engineers, Feb. 10, 2004, vol. 43, No. 2, pp. 133-138.

International Search Report and Written Opinion for International Patent Application Serial No. PCT/JP2018/007279 dated May 22, 2018.

Office Action dated Nov. 16, 2022, issued in corresponding Chinese patent application No. 201880015009.6 (original and English translation enclosed).

Liu et al., Three-dimensional Lower Limb Kinematic and Kinetic Analysis Based on a Wireless Sensor System, 2011 IEEE International Conference on Robotics and Automation, Aug. 18, 2011, pp. 842-847.

* cited by examiner

FIG.14A
FIG.14B
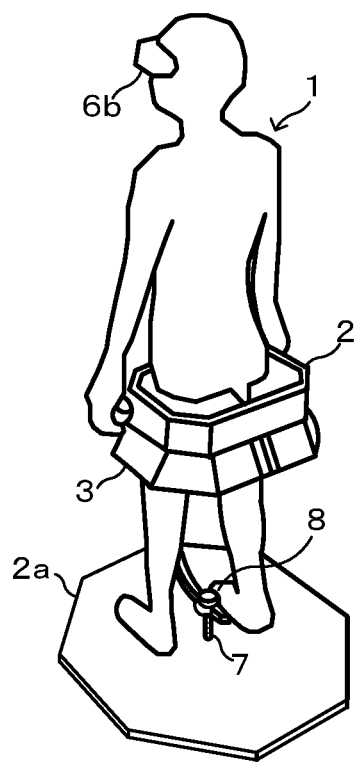
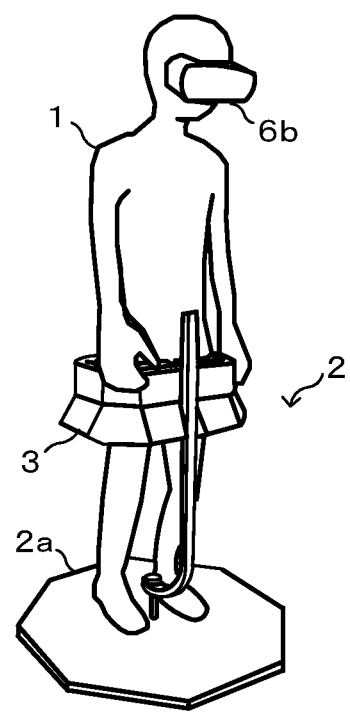

WALKING SENSE PRESENTATION DEVICE AND PRESENTATION METHOD

CROSS REFERENCE TO RELATED APPLICATION(S)

This application is a national phase filing of PCT/JP2018/007279, filed on Feb. 27, 2018, which claims priority to Japanese Patent Application No. 2017-038857, filed on Mar. 2, 2017, the entire disclosures of which are incorporated herein by reference.

TECHNICAL FIELD

The present disclosure relates to a walking sense presentation device and a presentation method capable of presenting walking sense at a fixed position.

BACKGROUND ART

There are treadmill type devices (see Patent Literature 1 and 2) that move on the ground in the opposite direction along with the movement of the feet of a user as a device that can obtain walking sense at a fixed position, and devices (see Patent Literature 3 and 4) that can obtain walking sense in any given front direction by rotating the treadmill. Furthermore, there are treadmills (see Patent Literature 5 and 6) that allow walking sideways by canceling movement not only in the front direction but also in all directions such as sides and diagonal directions.

As another configuration, there are foot pad type devices (see Patent Literature 7, 8 and 9) that simulate any ground by providing movable floors under the left and right feet and cause the floor to follow the feet.

As another configuration, there is a device (see Patent Literature 10) that generates walking sense by causing the femoral region to be alternately moved up and down.

Also, as a simplified method, there is a method (see Patent Literature 11) that converts stepping motion into walking motion in a simulated manner.

CITATION LIST

Patent Literature

Patent Literature 1: Japanese Patent No. 3550087
Patent Literature 2: Unexamined Japanese Patent Application Kokai Publication No. 2001-061992
Patent Literature 3: Japanese Patent No. 3200592
Patent Literature 4: Japanese Patent No. 4269646
Patent Literature 5: National Patent Publication No. 2000-516829
Patent Literature 6: Japanese Patent No. 3464976
Patent Literature 7: Unexamined Japanese Patent Application Kokai Publication No. 2008-220580
Patent Literature 8: Japanese Patent No. 3373460
Patent Literature 9: Japanese Patent No. 4313633
Patent Literature 10: Unexamined Japanese Patent Application Kokai Publication No. 2006-239086
Patent Literature 11: Unexamined Japanese Patent Application Kokai Publication No. 2001-296951

SUMMARY OF INVENTION

Technical Problem

In these conventional techniques, there remain problems such as requiring a large-scale device for presenting walking sense, and inability to present sufficient walking sense with a simple device.

An objective of the disclosure is to solve the problems of the conventional techniques, and to provide a walking sense presentation device and a presentation method excellent in walking sense with a compact device configuration.

Solution to Problem

In order to achieve the above objective, a walking sense presentation device according to the present disclosure includes:
a femoral region supporter that supports a femoral region of a user in a direction in which the user travels;
a first sensor that detects force received by the femoral region supporter from the femoral region of the user;
a walking motion estimator that estimates walking motion of the user based on the force detected by the first sensor;
a video generator that generates video to be presented to the user based on the walking motion estimated by the walking motion estimator; and
a video presenter that presents the video generated by the video generator to the user.

The walking sense presentation device according to the present disclosure further includes:
a rotation mechanism that rotatably supports the femoral region supporter; and
a second sensor that detects a rotation angle of the femoral region supporter by the rotation mechanism.

The walking sense presentation device according to the present disclosure further includes a third sensor that detects a posture of the user.

In order to achieve the above objective, a walking sense presentation method according to the present disclosure includes:
a first detection step of supporting, by a femoral region supporter, a femoral region of a user in a direction in which the user travels, and detecting force received by the femoral region supporter from the femoral region of the user;
an estimation step of estimating, by a calculator, walking motion of the user based on the force detected by a first sensor;
a video generation step of generating, by the calculator, video to be presented to the user based on the walking motion estimated; and
a video presentation step of presenting the generated video to the user.

The walking sense presentation method according to the present disclosure further includes:
a second detection step of allowing the femoral region supporter to be rotatable, and detecting, by a second sensor, a rotation angle of the femoral region supporter;
wherein, in the video generation step, the video to be presented to the user is generated based on the rotation angle in a travel direction of the user detected in the second detection step.

The walking sense presentation method according to the present disclosure further includes:
a third detection step of detecting, by a third sensor, a posture of the user, wherein, in the video generation step, the video to be presented to the user is generated according to change of the posture of the user detected in the third detection step.

Advantageous Effects of Invention

According to a walking sense presentation device of the present disclosure, a femoral region of a user is supported in travel direction to cause a change in the center of gravity in the travel direction, and the walking sense is presented by presenting a video according to walking motion of a user. As a result, a compact and lightweight device can be realized inexpensively without the need for a large-scale device that moves the floor in accordance with the movement of the feet and a drive unit that raises and lowers the femoral region.

Furthermore, according to the walking sense presentation device of the present disclosure, a better walking sense can be presented by detecting the change in the travel direction or the posture of the user and changing the video presented to the user according to the detection result.

BRIEF DESCRIPTION OF DRAWINGS

FIG. 14A is a perspective view illustrating a case where a user uses a head-mounted video presentation device as a walking sense presentation device of FIG. 13;

FIG. 14B is a perspective view illustrating the case where a user turns in another direction in the walking sense presentation device of FIG. 14A;

DESCRIPTION OF EMBODIMENTS

Figure 1:
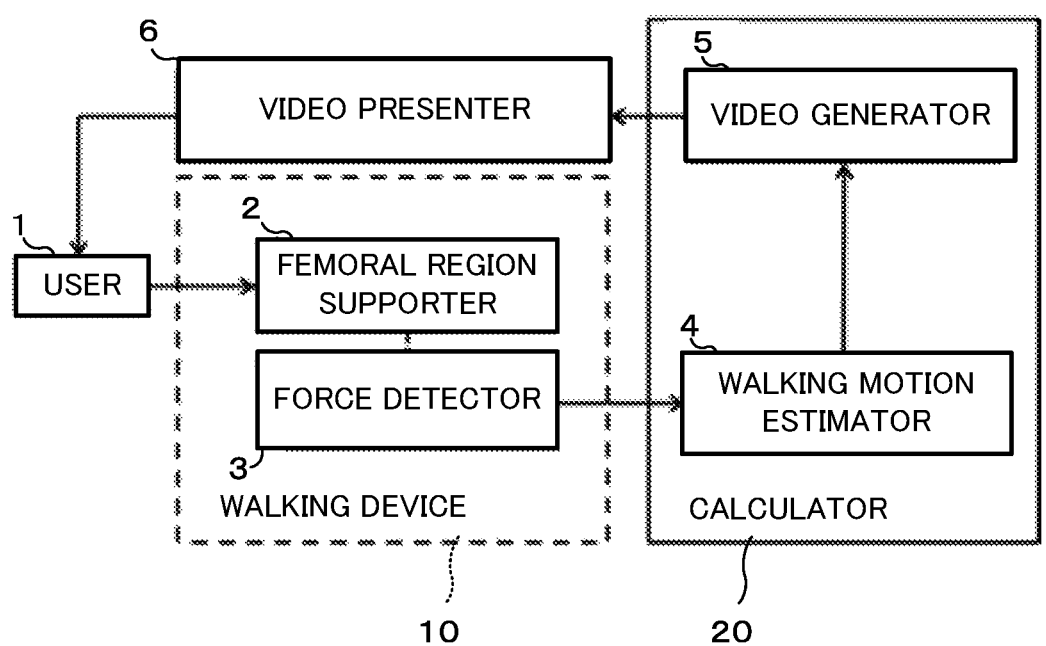
FIG. 1 is a block diagram illustrating a configuration of a walking sense presentation device according to Embodiment 1 of the present disclosure.

Hereinafter, embodiments of the present disclosure will be described with reference to drawings. The same or similar reference numerals are given to the same or similar portions in the description of the drawings.

Embodiment 1

As illustrated in FIG. 1, the walking sense presentation device according to Embodiment 1 of the present disclosure includes a femoral region supporter 2, a force detector 3 as a first sensor, a walking motion estimator 4, a video generator 5, and a video presenter 6. The femoral region supporter 2 supports the femoral region of a user 1 in the direction in which the user 1 travels. The force detector 3 detects force received by the femoral region supporter 2 from the femoral region of the user 1. The walking motion estimator 4 estimates the walking motion of the user 1 based on the force detected by force detector 3. The video generator 5 generates a video to be presented to the user 1 based on the walking motion estimated by the walking motion estimator 4. The video presenter 6 presents the video generated by the video generator 5 to the user 1. Here, "presenting video" means displaying a video so that the user 1 can see the video.

It should be noted that the femoral region supporter 2 and the force detector 3 can be summarized as a walking device 10 which is a man-machine interface with the user 1. Also, the walking motion estimator 4 and video generator 5 are realized on a calculator 20. The calculator 20 is a computer including a CPU, a memory, and a storage. The functions of the walking motion estimator 4 and the video generator 5 are realized by the CPU executing the program stored in the memory.

Figure 2A:
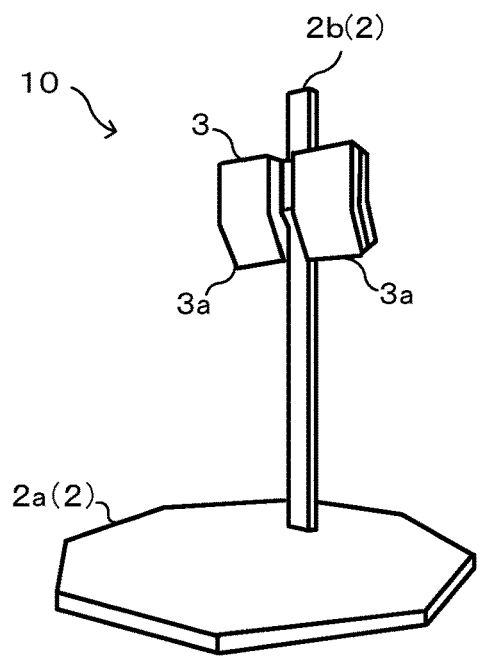
FIG. 2A is a perspective view illustrating an example of appearance of the walking sense presentation device according to Embodiment 1 of the present disclosure.
Figure 2B:
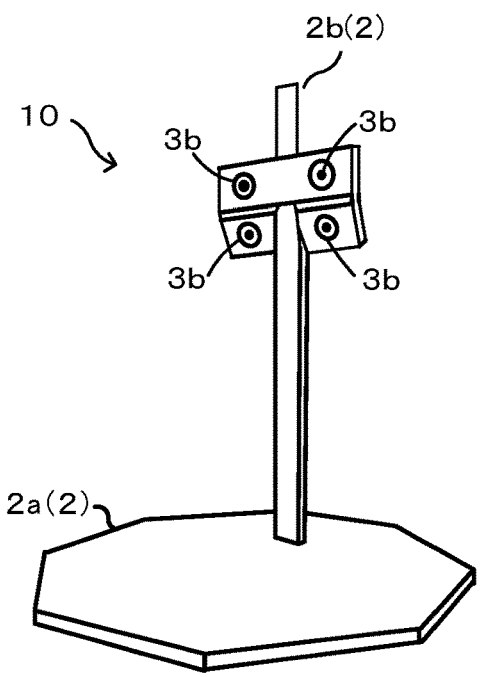
FIG. 2B is a perspective view illustrating an internal structure of part of the walking sense presentation device of FIG. 2A.
Figure 2C:
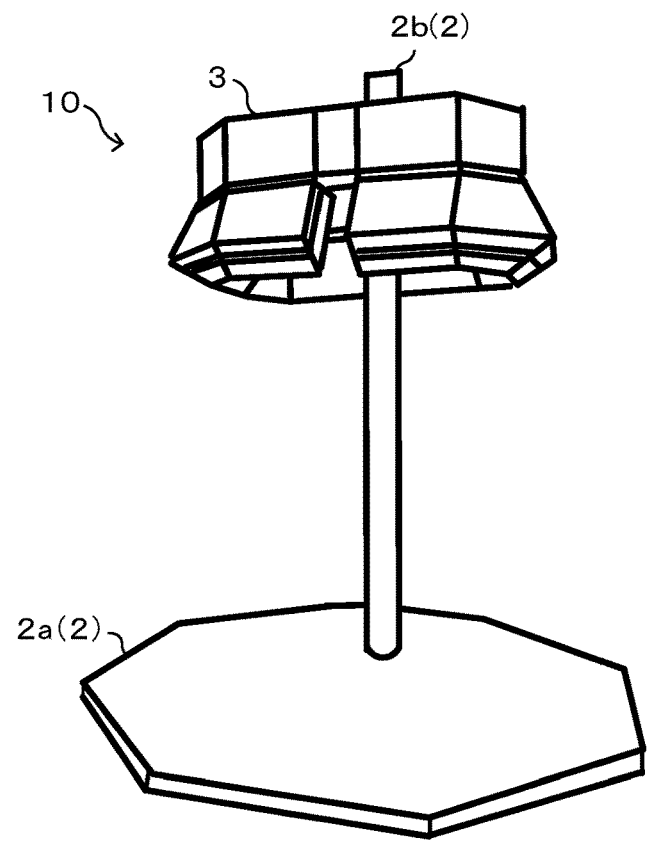
FIG. 2C is a perspective view illustrating another configuration of the walking sense presentation device.

FIGS. 2A to 2C are perspective views illustrating the actual configuration of the walking device 10. FIG. 2A illustrates the appearance of the walking device 10. This walking device 10 detects the walking motion when the user 1 walks in the front direction. FIG. 2B illustrates the internal structure of a part of the walking device 10 of FIG. 2A. FIG. 2C illustrates the appearance of the walking device 10 walking in all directions. As illustrated in FIG. 2A, the femoral region supporter 2 includes a base 2a and a support pillar 2b. The force detector 3 is fixed by the base 2a and the support pillar 2b in order to support the femoral region in the direction of travel of the user 1. As illustrated in FIG. 2B, the force detector 3 includes femoral region contact portions 3a and force sensors 3b. The femoral region contact portion 3a is a portion where the femoral region of the user 1 contacts the device. The force sensors 3b are provided in the femoral region contact portion 3a, and detect the force received from the femoral region of the user 1.

As illustrated in FIG. 2B, the force detector 3 is arranged with force sensors 3b in at least a part where the femoral region upper portion contacts and a part where the femoral region lower portion contacts when the user 1 raises the femoral region in order to estimate the posture of the femoral region when the user 1 is in a forwardly-bent posture in the travel direction and performs walking motion.

Also, in a case where the femoral region supporter 2 is perpendicular to the travel direction of the user 1, the force sensor 3b of the femoral region lower portion is likely to respond even when the user 1 does not raise the femoral region, and therefore, the femoral region supporter 2 is desirable to be angled so that the force sensor 3b of the femoral region lower portion does not respond to the travel direction of the user 1. It is desirable that the angle at this time can be adjusted to an angle (about 10 to 60 degrees) at which the femoral region rises when the user 1 actually walks. In addition, it is desirable to use a shock absorbing material such as sponge for the femoral region contact portion 3a, since the reaction force received from the force detector 3 may feel uncomfortable when the user 1 raises the femoral region. When the user 1 walks in all directions, the force detector 3 is arranged around the femoral region of the user 1 as illustrated in FIG. 2C. It should be noted that the force detector 3 may be fixed to the femoral region supporter 2 or attached to the user 1.

Figure 3A:
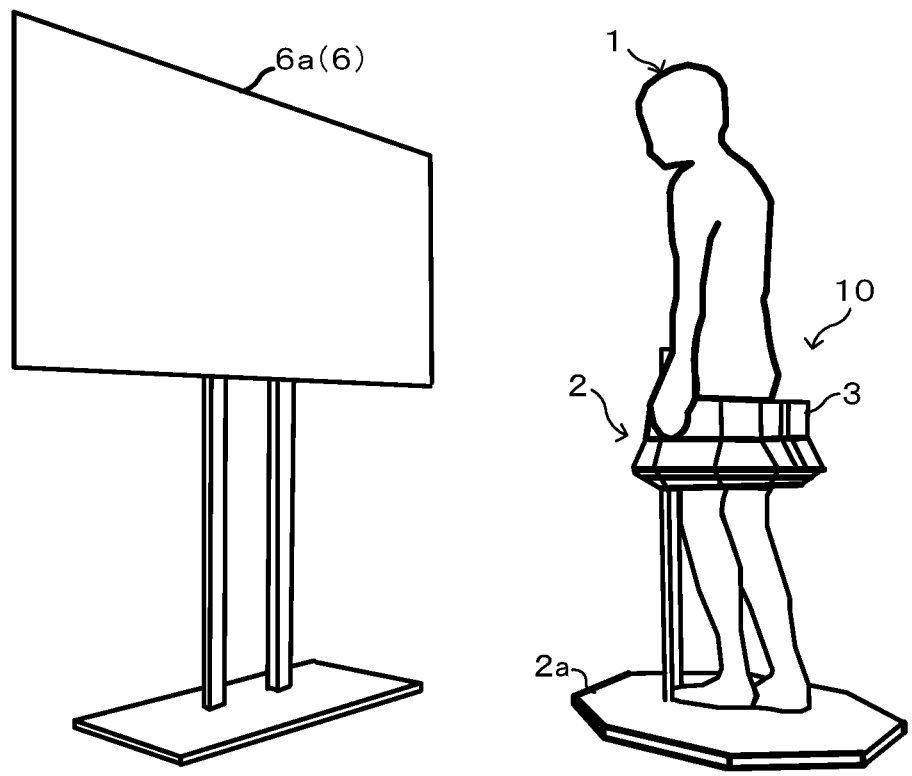
FIG. 3A is a perspective view illustrating a case where a user uses a stationary video presentation device as the walking sense presentation device of FIG. 1.
Figure 3B:
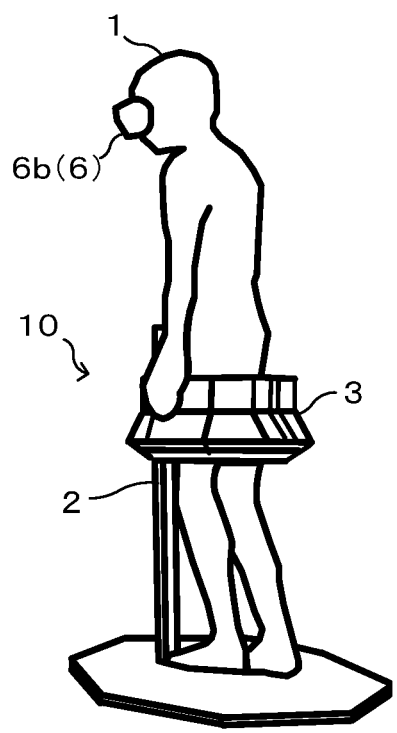
FIG. 3B is a perspective view illustrating a case where a user uses a head-mounted video presentation device as the walking sense presentation device of FIG. 1.

FIGS. 3A and 3B are each a view illustrating that the user 1 is actually using the walking sense presentation device of FIG. 1. FIG. 3A illustrates a case where the stationary video presentation device 6a illustrated in FIG. 2C is used as the video presenter 6. FIG. 3B is a case where head-mounted video presentation device 6b is used as the video presenter 6.

The user 1 stands on the base 2a for supporting the femoral region in the travel direction. Then, the user 1 performs walking motion while taking a bent posture in the direction in which the user 1 wants to proceed with respect to the femoral region supporter 2. This walking motion causes a change in the center of the gravity of the user 1 in the travel direction. Since the femoral region is supported in the travel direction by the femoral region supporter 2, the force detector 3 detects the force received from the femoral region of the user 1. The walking motion estimator 4 estimates the walking motion of the user 1 based on the force detected by force detector 3. The video generator 5 generates a video according to the estimated walking motion and displays the video on the video presenter 6, whereby the walking sense is presented to the user 1. In the case of FIG. 3A, the video is presented on the screen of the stationary video presentation device 6a, and in the case of FIG. 3B, the video is presented on the head-mounted video presentation device 6b.

Figure 4A:
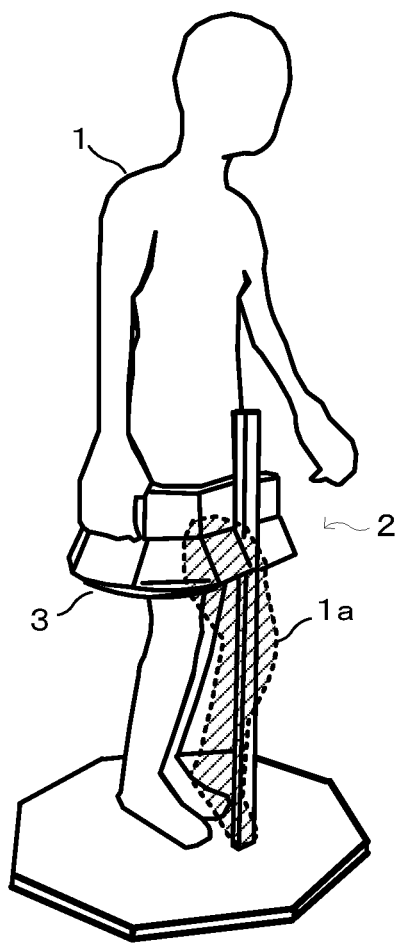
FIG. 4A is a perspective view illustrating a walking posture of the user, particularly in a case where the posture of the right foot is estimated when the user walks forward.
Figure 4B:
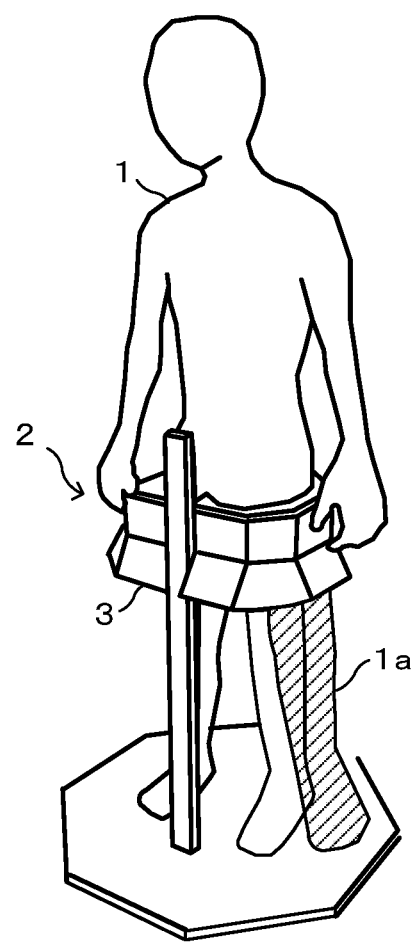
FIG. 4B is a perspective view illustrating a walking posture of the user, particularly in a case where the posture of the left foot is estimated when the user walks sideways.

FIGS. 4A and 4B each illustrate how the walking motion estimator 4 estimates the walking posture of the user 1 while the user 1 is actually using the walking sense presentation device of FIG. 1. As illustrated in FIG. 4A, when the user 1 performs walking motion in the front direction, and the force sensor 3b of the force detector 3 detects a force received from the femoral region, the walking motion estimator 4 estimates the posture of the femoral region of the right foot that does not actually come forward, i.e., estimates a walking posture 1a to be estimated. As illustrated in FIG. 4B, when the user 1 performs a walking motion in the lateral direction, the walking motion estimator 4 estimates a posture of the femoral region of the left foot that does not actually come left, i.e., estimates a walking posture 1a to be estimated.

Figure 5:
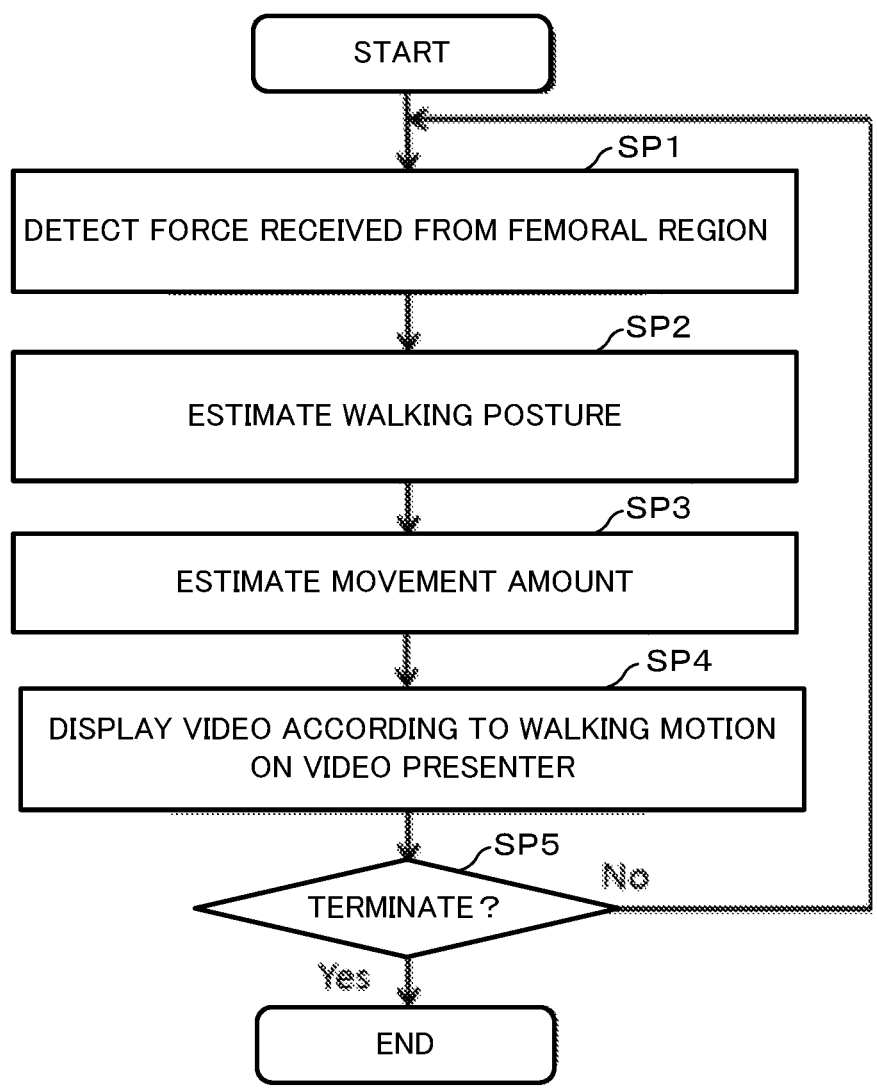
FIG. 5 is a flowchart illustrating a motion procedure of the walking sense presentation device according to Embodiment 1 of the present disclosure.

Motion procedure of the walking sense presentation device of FIG. 1 will be explained with reference to FIG. 5.

(A) The force detector 3 detects the force that the femoral region supporter 2 receives from the femoral region of the user 1, and transmits it to the calculator 20 (step SP1; first detection step).

(B) The walking motion estimator 4 of calculator 20 estimates the bent posture and the posture of the femoral region of the user 1 based on the received detection value of force detector 3 (step SP2; estimation step), and estimates the movement amount of the user 1 on the basis of the estimated walking posture 1a (step SP3).

(C) The video generator 5 of the calculator 20 generates a video to be displayed on the video presenter 6 based on the estimated movement amount in the travel direction of the user 1, and causes the video presenter 6 to display the generated video (step SP4; video generation step, video presentation step).

(D) Finally, the walking sense presentation device determines whether or not a predetermined termination instruction is given (step SP5), and in a case where the termination instruction is given (step SP5; Yes), the walking sense presentation device terminates the operation, and in a case where the termination instruction is not given (step SP5; No), the walking sense presentation device returns to step SP1.

As described above, when the user 1 performs walking motion on the walking sense presentation device of FIG. 1, the femoral region is supported by the femoral region supporter 2, and accordingly, the walking motion in the travel direction causes a change in the center of the gravity of the user 1. At this time, the walking motion estimator 4 estimates the walking motion of the user 1 based on the detection value of the force sensor 3b provided in the force detector 3, and the video generator 5 generates a video according to the walking motion, and the video presenter 6 displays the generated video. The user 1 who sees this video can feel the walking sense even though the user 1 is not actually walking.

According to Embodiment 1, as illustrated in FIG. 2C, the force detector 3 is arranged in the travel direction of the user 1, and the femoral region of the user 1 is supported. The user 1 can easily obtain walking sense in all directions by performing walking motion while taking bent posture in the travel direction.

In addition, according to the walking sense presentation device of Embodiment 1, the walking motion is performed only by the force of the user 1 himself/herself, and no external force is added to the body of the user 1. This enables safe use of the walking sense presentation device.

The walking sense presentation device according to Embodiment 1 can be used for rehabilitation for the purpose of functional recovery of the walking exercise for the user 1 when the user 1 has a gait disorder, and for improving exercise capability for the elderly with weak legs and healthy people.

Embodiment 2

Figure 6:
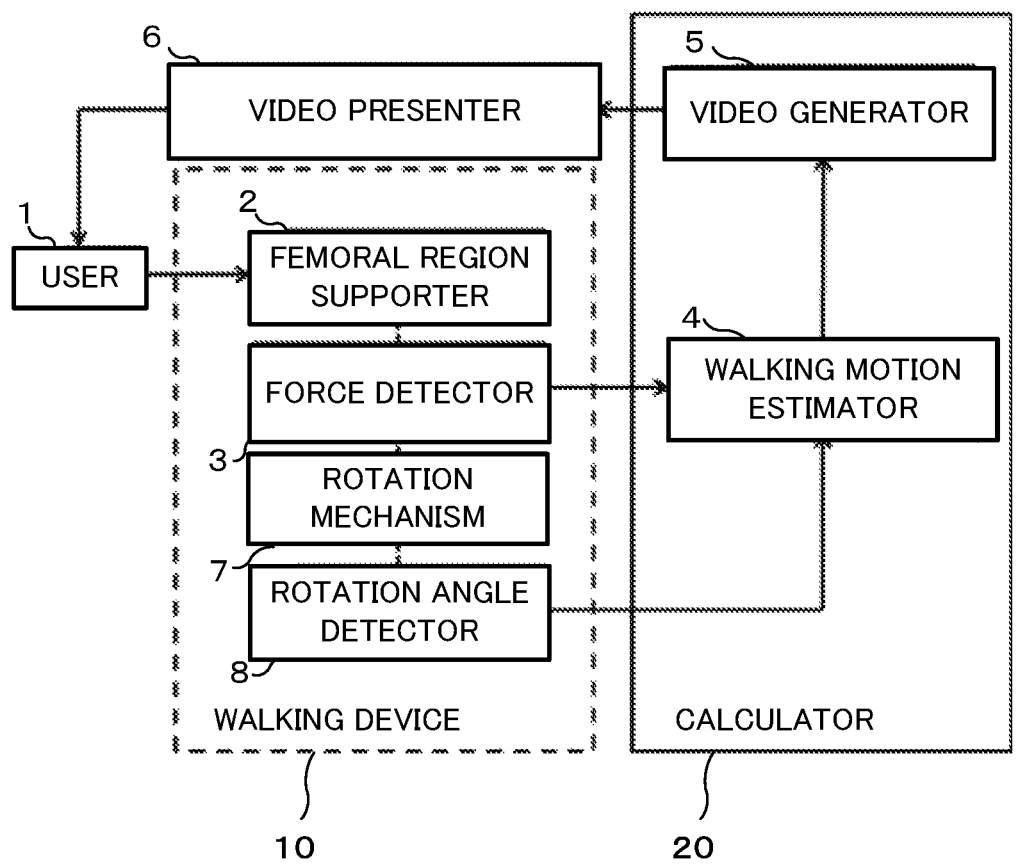
FIG. 6 is a block diagram illustrating a configuration of a walking sense presentation device according to Embodiment 2 of the present disclosure.

Next, Embodiment 2 of the present disclosure will be described. As illustrated in FIG. 6, in addition to the configuration of the walking sense presentation device according to Embodiment 1, the walking sense presentation device according to Embodiment 2 includes, as constituent elements of the walking device 10, a rotation mechanism 7 and a rotation angle detector 8 as a second sensor. The rotation mechanism 7 supports the femoral region supporter 2 rotatably in any horizontal direction. In addition, the rotation angle detector 8 detects the rotation angle of the femoral region supporter 2 by the rotation mechanism 7. By providing the rotation mechanism 7 and the rotation angle detector 8, the user 1 can turn around in any direction in the horizontal plane.

Figure 7A:
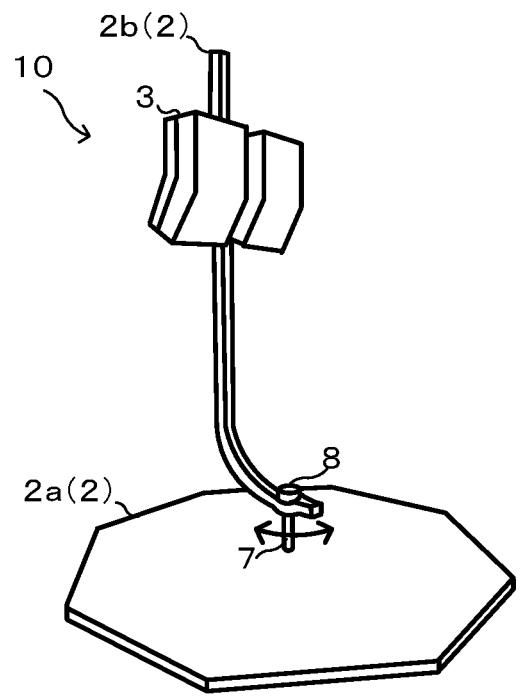
FIG. 7A is a perspective view illustrating appearance of a walking sense presentation device according to Embodiment 2 of the present disclosure.
Figure 7B:
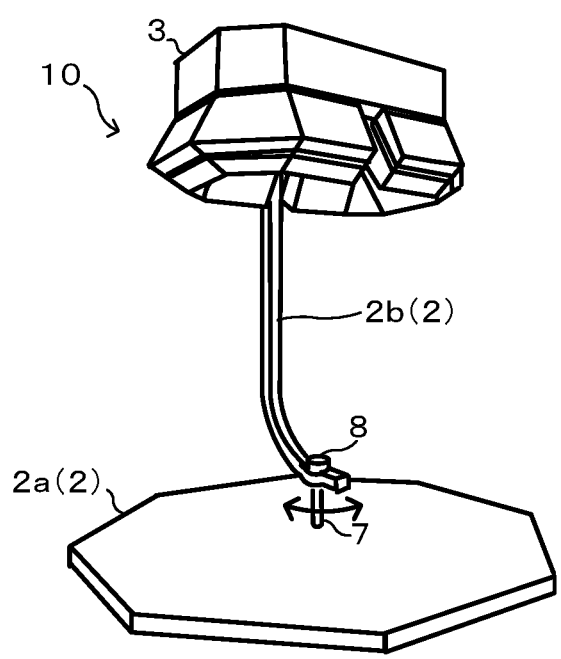
FIG. 7B is a perspective view illustrating another configuration of the walking sense presentation device according to Embodiment 2 of the present disclosure.

FIGS. 7A and 7B are each a perspective view illustrating the actual configuration of the portion surrounded by a dotted line of the walking sense presentation device of FIG. 6. FIG. 7A illustrates the appearance of the walking sense presentation device when only walking in an arbitrary front direction. FIG. 7B illustrates the appearance of the walking sense presentation device when walking in all directions in an arbitrary front direction. As illustrated in FIG. 7A and FIG. 7B, the rotation mechanism 7 and the rotation angle detector 8 are provided in the femoral region supporter 2. The rotation mechanism 7 and the rotation angle detector 8 may be mounted on the side of the base 2a or on the side of the support pillar 2b. As the rotation angle detector 8, a rotation angle sensor, an optical camera, an inertial sensor or the like can be used. The other points are the same as those of the above-described Embodiment 1 (see FIGS. 2A, 2B, 2C), and the explanation will be omitted.

Figure 8A:
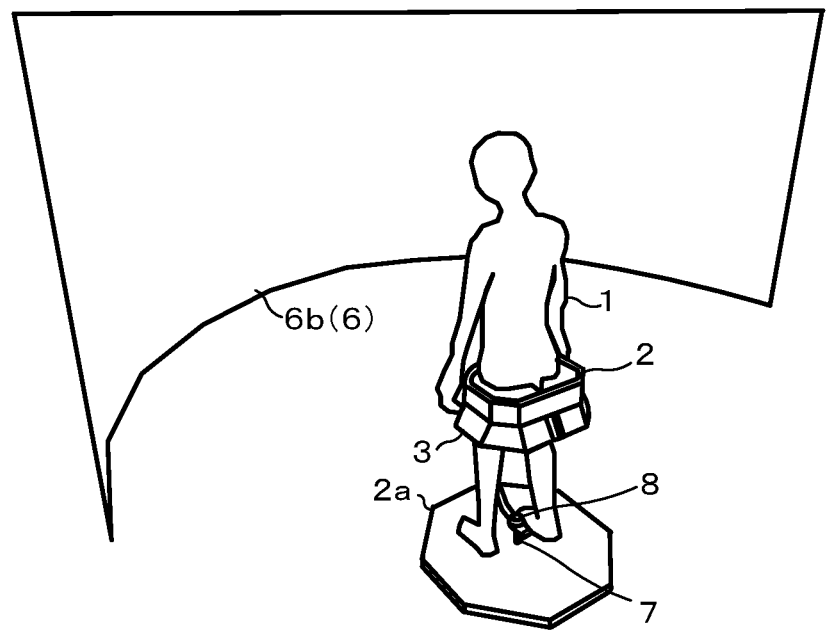
FIG. 8A is a perspective view illustrating a case where a user uses a stationary video presentation device as the walking sense presentation device of FIG. 6.
Figure 8B:
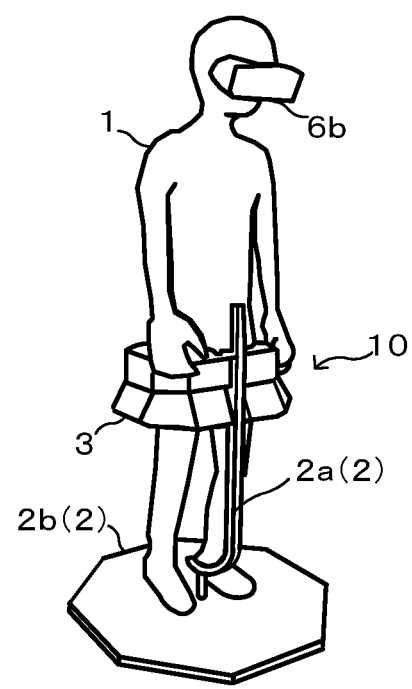
FIG. 8B is a perspective view illustrating a case where a user uses a head-mounted video presentation device as the walking sense presentation device of FIG. 6.

FIGS. 8A and 8B are each a diagram illustrating that the user 1 is actually using the walking sense presentation device of FIGS. 7A and 7B. In FIG. 8A, the stationary video presentation device 6a is used as the video presenter 6, and in FIG. 8B, the head-mounted video presentation device 6b is used as the video presenter 6. As illustrated in FIG. 8A and FIG. 8B, the rotation mechanism 7 allows the user 1 to rotate the femoral region supporter 2 in any direction. The rotation angle detector 8 detects the rotation angle of the femoral region supporter 2, and the force detector 3 detects the force received from the femoral region of the user 1, and the walking motion estimator 4 detects the front direction of the user 1 and the walking motion, video generator 5 generates a video according to the estimated walking motion and displays the generated video on the video presenter 6. The user 1 who sees this video can feel the walking sense even though the user 1 is not actually walking.

Figure 9:
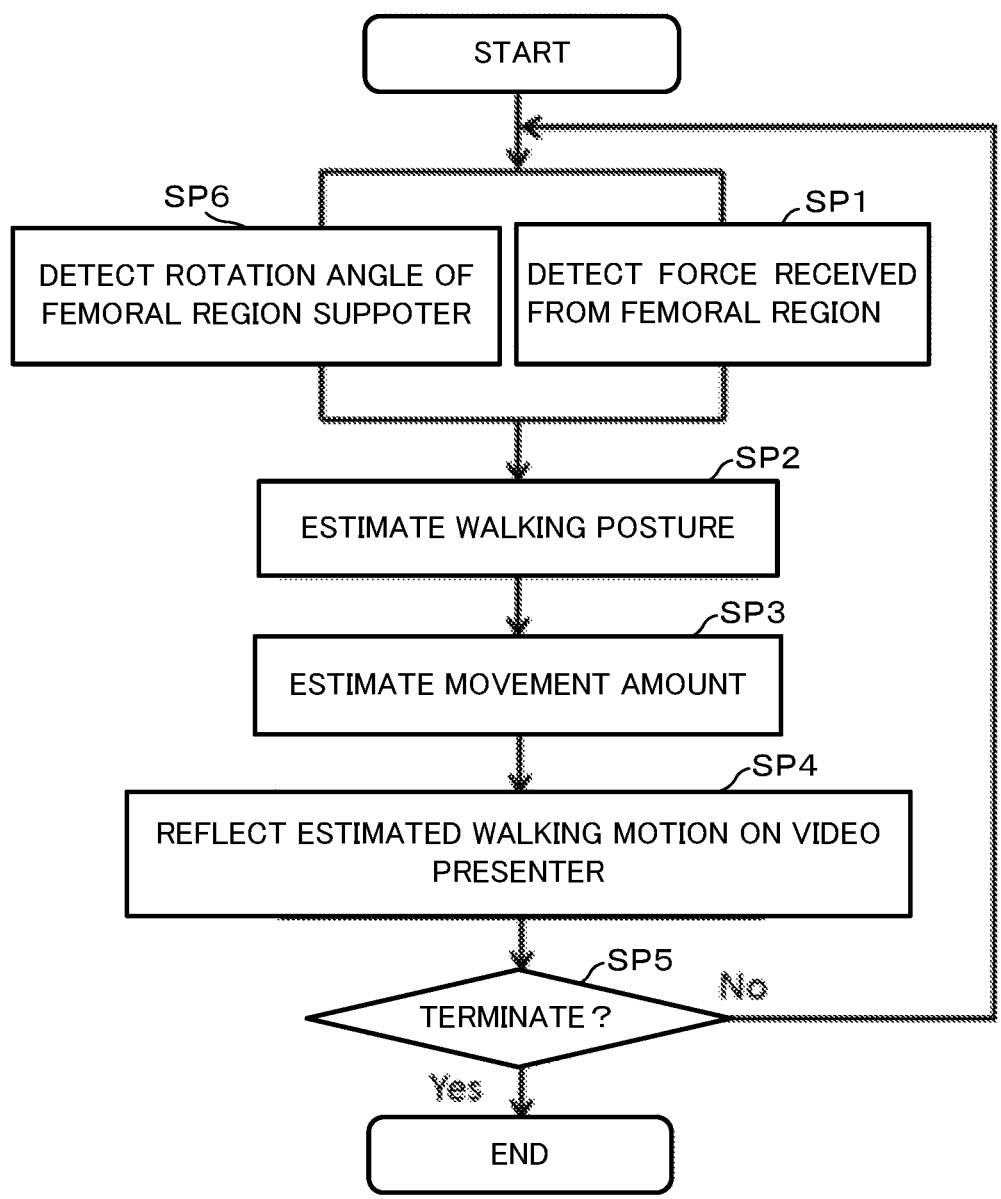
FIG. 9 is a flowchart illustrating a motion procedure of the walking sense presentation device according to Embodiment 2 of the present disclosure.

Motion procedure of the walking sense presentation device of FIG. 6 will be explained with reference to FIG. 9.

(A) The rotation angle detector 8 detects the rotation angle of the femoral region supporter 2 and transmits it to the calculator 20 (step SP6; second detection step).

(B) The force detector 3 detects the force that the femoral region supporter 2 receives from the femoral region of the user, and transmits it to the calculator 20 (step SP1). (A) and (B) are performed simultaneously.

(C) The walking motion estimator 4 of the calculator 20 calculates the front direction of the user 1 based on the received rotation angle of the femoral region supporter 2, and estimates the bent posture of the user 1 and the posture of the femoral region of the user 1 based on the detection of force detector 3 received (step SP2). Furthermore, the walking motion estimator 4 of the calculator 20 estimates the movement amount of the user 1 based on the estimated walking posture 1a (step SP3).

(D) The calculator 20 generates a video to be displayed on the video presenter 6 based on the estimated movement amount in the travel direction of the user, and causes the video presenter 6 to display the generated video (step SP4).

(E) The walking sense presentation device determines whether or not a predetermined termination instruction is given (step SP5), and in a case where the termination instruction is given (step SP5; Yes), the walking sense presentation device terminates the motion, and in a case where the termination instruction is not given (step SP5; No), the walking sense presentation device returns to steps SP1 and SP6.

As described above, when the user 1 performs walking motion on the walking sense presentation device, the femoral region is supported by the femoral region supporter 2, and accordingly, the walking motion in the travel direction causes a change in the center of the gravity of the user 1. Also, the user 1 can freely change the front direction by the rotation mechanism 7. At this time, based on the detection of the rotation angle detector 8 and the force detector 3 (force sensor 3b), the walking motion estimator 4 estimates the walking motion of the user 1, and the video generator 5 generates a video according to the walking motion, and display the video on the video presenter 6. By doing this, it becomes possible to give the user 1 a walking sense in any front direction.

Embodiment 3

Figure 10:
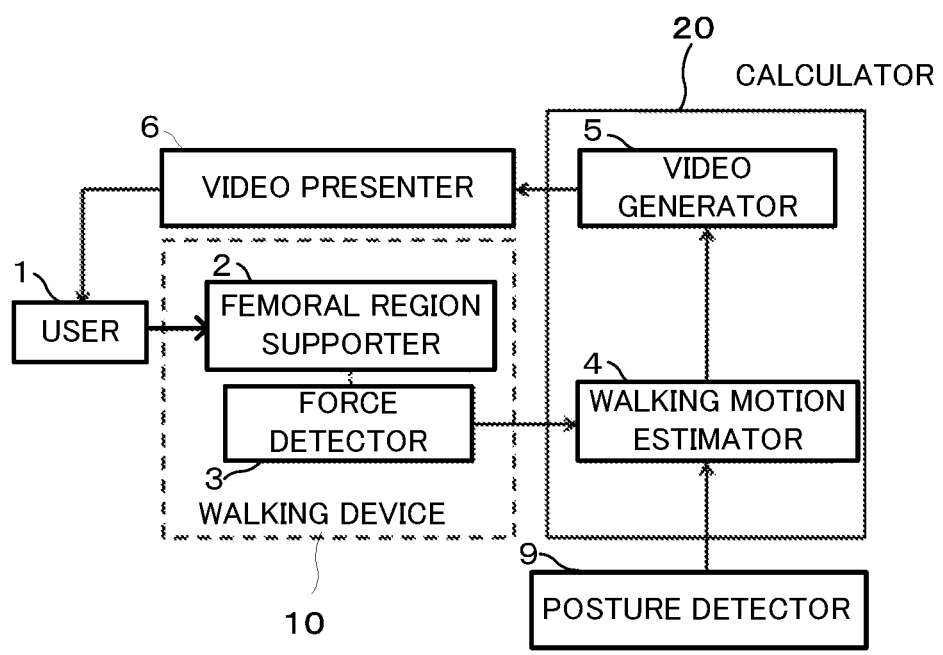
FIG. 10 is a block diagram illustrating a configuration of a walking sense presentation device according to Embodiment 3 of the present disclosure.

Next, Embodiment 3 of the present disclosure will be described. As illustrated in FIG. 10, a walking sense presentation device according to Embodiment 3 is different from the above Embodiment 1 in that the walking sense presentation device further comprises a posture detector 9 as a third sensor for detecting the posture of the user 1. By providing the posture detector 9, the user 1 can obtain more realistic walking sense in any direction.

Figure 11A:
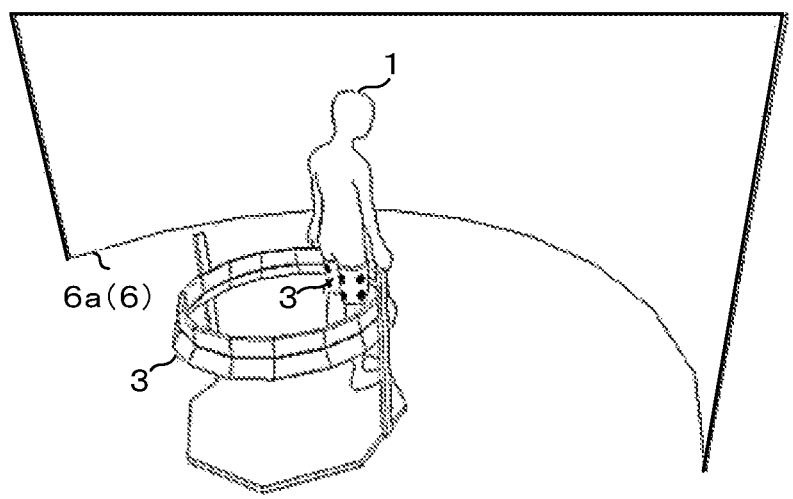
FIG. 11A is a perspective view illustrating a case where a user uses a stationary video presentation device as a walking sense presentation device of FIG. 10.
Figure 11B:
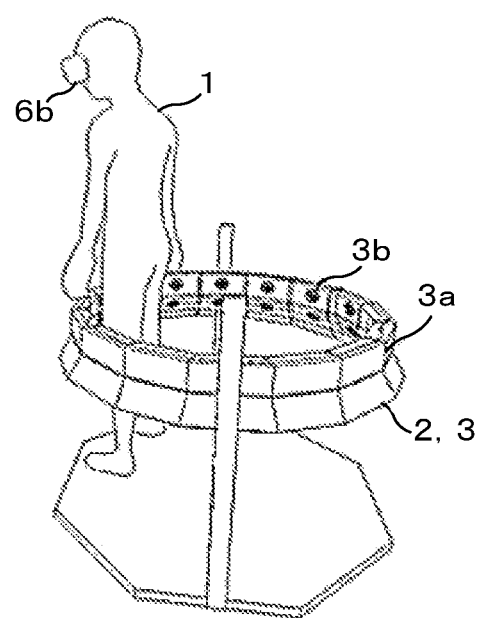
FIG. 11B is a perspective view illustrating a case where a user uses a head-mounted video presentation device as a walking sense presentation device of FIG. 10.

FIGS. 11A and 11B are each a diagram illustrating a state in which the user 1 is actually using the walking sense presentation device of FIG. 10. In FIG. 11A, a stationary video presentation device 6a is used as the video presenter 6. In FIG. 11B, a head-mounted video presentation device 6b is used as the video presenter 6. The force detector 3 is provided in the femoral region supporter 2. As the posture detector 9, an optical camera, an inertial sensor, an angle sensor, and the like, not shown, can be used. The posture information detected by the posture detector 9 is used for the walking posture of the walking motion estimator 4 and the estimation of the movement amount, and the change in the posture of the user 1 is reflected in the video presented by the video presenter 6. The user 1 can obtain walking sense while looking in any direction by performing motion while looking at the video. In the present embodiment, when the user 1 contacts the femoral region supporter 2, the walking sense according to the estimated walking motion is given to the user 1, and when the user 1 does not contact the femoral region supporter 2, an actual walking sense can be obtained. Also, even when the femoral region supporter 2 is not touched, it is possible to change the video according to the motion such as sitting motion or jumping, to obtain the feeling of actually sitting or jumping.

Figure 12:
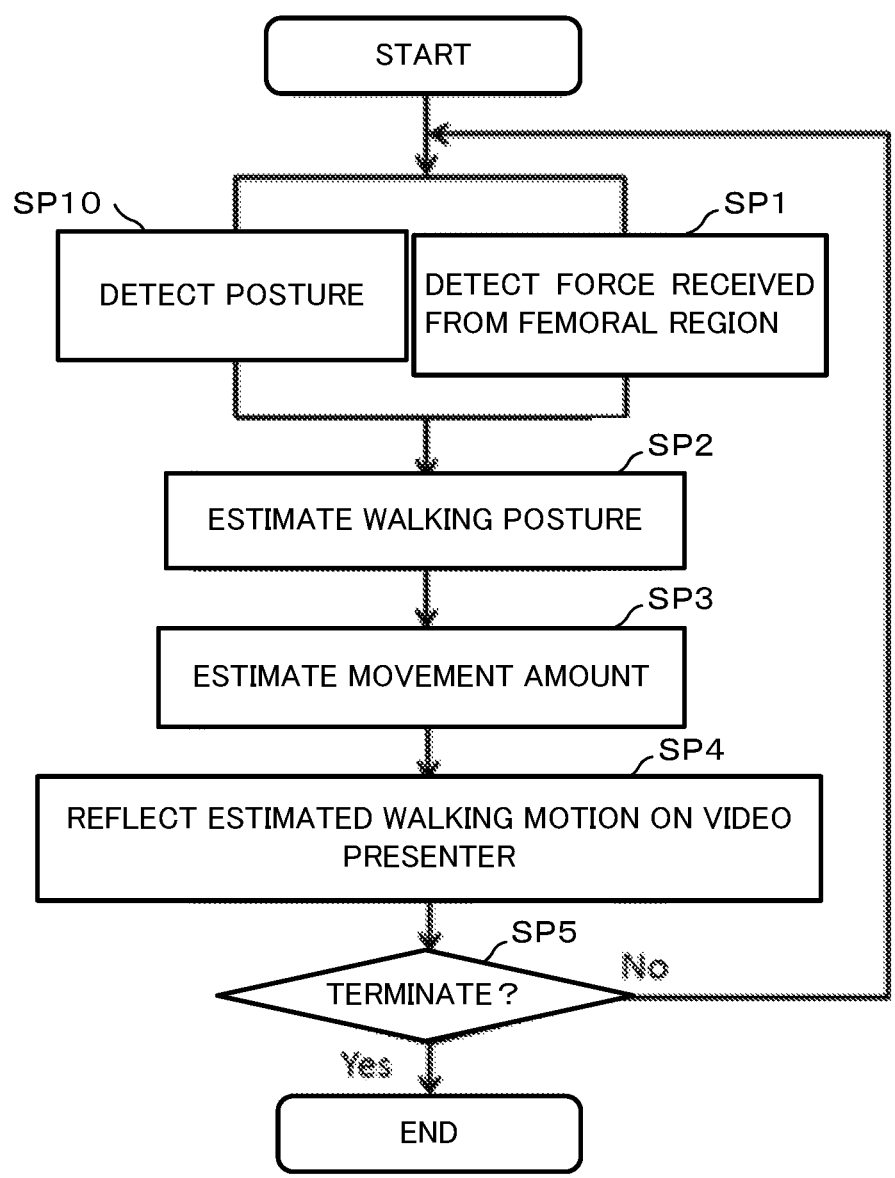
FIG. 12 is a flowchart illustrating a motion procedure of the walking sense presentation device according to Embodiment 3 of the present disclosure.

Motion procedure of the walking sense presentation device according to the present embodiment will be described with reference to FIG. 12.

(A) The posture detector 9 detects the posture of the user 1 and transmits it to the calculator 20 (step SP10; third detection step).

(B) The force detector 3 detects the force that the femoral region supporter 2 receives from the femoral region of the user 1, and transmits it to the calculator 20 (step SP1). (A) and (B) are performed simultaneously.

(C) The walking motion estimator 4 of the calculator 20 estimates the walking posture of the user 1 based on the received bent posture of the user 1 and the force received from the femoral region (step SP2). Furthermore, the walking motion estimator 4 of the calculator 20 estimates the movement amount of the user 1 based on the estimated walking posture (step SP3).

(D) The video generator 5 of the calculator 20 generates a video to be displayed on the video presenter 6 based on the estimated movement amount in the travel direction of the user 1, and causes the video presenter 6 to display the generated video (step SP4).

(E) The walking sense presentation device determines whether or not a predetermined termination instruction is given (step SP5), and in a case where the termination instruction is given (step SP5; Yes), the walking sense presentation device terminates the motion, and in a case where the termination instruction is not given (step SP5; No), the walking sense presentation device returns to steps SP1 and SP10.

As described above, when the user 1 performs walking motion on the walking sense presentation device, a video according to the walking motion is presented to the user 1 based on the force received from femoral region of the user 1 and the posture of the user 1. In this way, when the walking motion is performed while taking a bent posture in the contact direction, it is possible to obtain walking sense associated with the walking motion. In addition, even when the femoral region of the user 1 does not contact the femoral region supporter 2, the user 1 can feel a realistic motion sensation by presenting a video according to the motion such as sitting motion or jumping.

Embodiment 4

Figure 13:
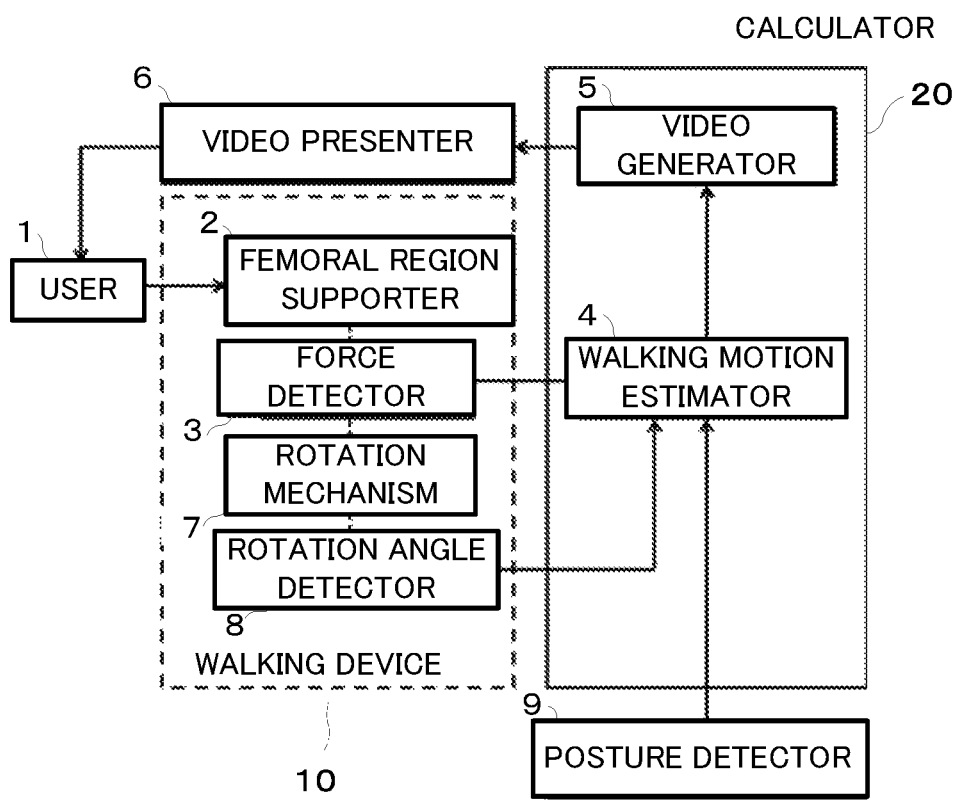
FIG. 13 is a block diagram illustrating a configuration of a walking sense presentation device according to Embodiment 4 of the present disclosure.

Next, Embodiment 4 according to the present disclosure will be described. The walking sense presentation device according to Embodiment 4 is different from Embodiment 2 in that a walking sense presentation device according to Embodiment 4 includes a posture detector 9 for detecting the posture of the user 1 as illustrated in FIG. 13. This allows the user 1 to obtain more realistic walking sense in any direction.

FIGS. 14A and 14B each illustrate how the user 1 is actually using the walking sense presentation device of FIG. 13. In FIG. 14A, a head-mounted video presentation device 6b is used as the video presenter 6. In FIG. 14B, the user 1 turns in a direction different from that of FIG. 14A. With the posture detector 9, the user 1 can obtain walking sense in any direction.

Figure 15:
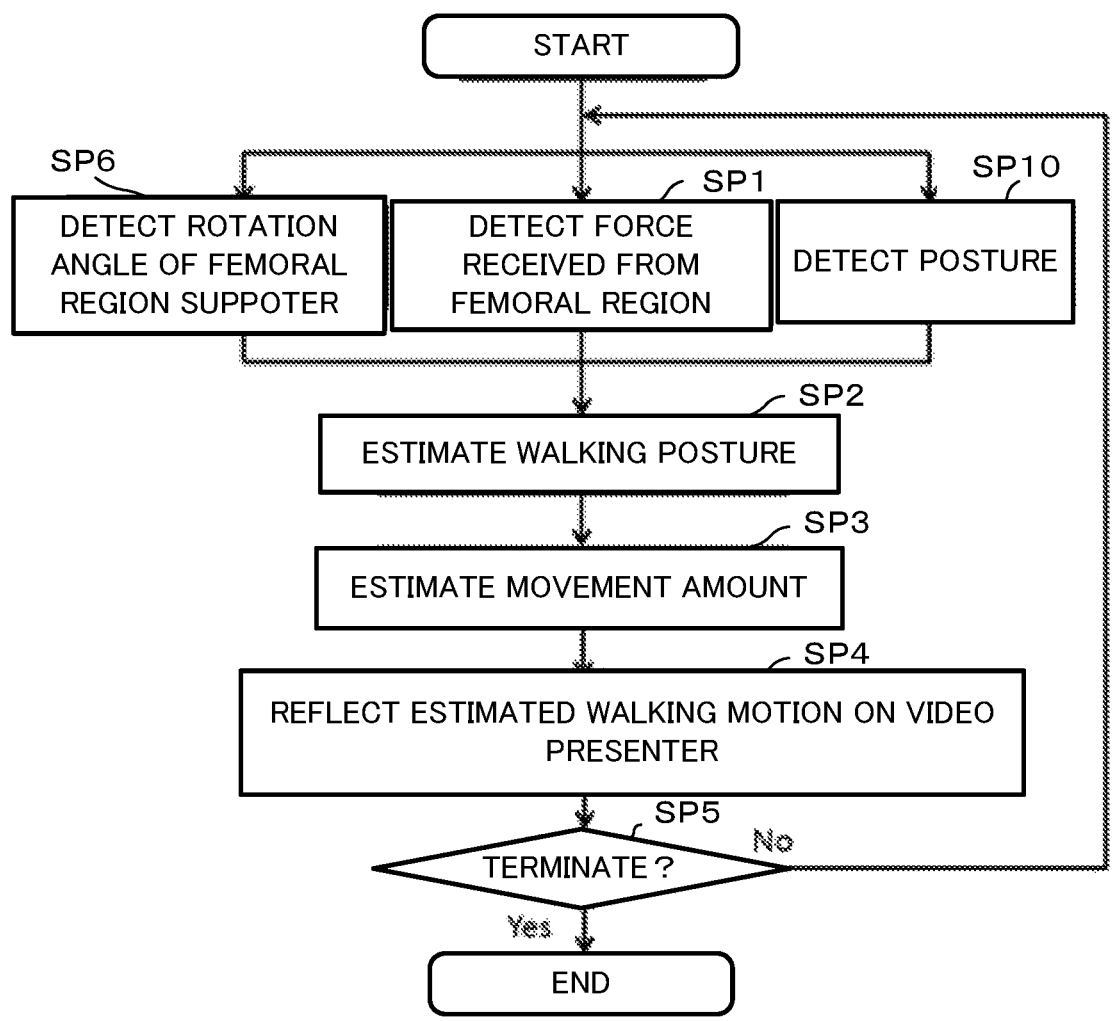
FIG. 15 is a flowchart illustrating a motion procedure of the walking sense presentation device according to Embodiment 4 of the present disclosure.

Motion procedure of the walking sense presentation device will be explained with reference to FIG. 15.

(A) The rotation angle detector 8 detects the rotation angle of the femoral region supporter 2 and transmits it to the calculator 20 (step SP6).

(B) The force detector 3 detects the force that the femoral region supporter 2 receives from the femoral region of the user 1, and transmits it to the calculator 20 (step SP1).

(C) The posture detector 9 detects the posture of the user and transmits it to the calculator 20 (step SP10; third detection step). (A), (B) and (C) are performed simultaneously.

(D) The walking motion estimator 4 of the calculator 20 estimates the walking posture of the user 1 based on the rotation angle of femoral region supporter 2, the posture of the user 1, and the force received from the femoral region, and estimates the movement amount based on the estimated walking posture (step SP3).

(E) The walking motion estimator 4 of the calculator 20 generates a video to be displayed on the video presenter 6 based on the estimated movement amount of the user 1, and causes the video presenter 6 to display the generated video (step SP4).

(F) The walking sense presentation device determines whether or not a predetermined termination instruction is given (step SP5), and in a case where the termination instruction is given (step SP5; Yes), the walking sense presentation device terminates the motion, and in a case where the termination instruction is not given (step SP5; No), the walking sense presentation device returns to steps SP1, SP6 and SP10.

As described above, according to the present embodiment, the video according to the walking motion estimated by the force detector 3, the rotation angle detector 8, and the posture detector 9 is presented to the user 1. In this way, in a case where the user 1 performs walking motion while taking a bent posture in the travel direction, a video matched to the walking motion is presented to the user 1 and thus a walking sense associated with the walking motion can be obtained.

EXAMPLES

In order to show the implementability of the present disclosure, concrete experiment data (for example, detection data with the force detector 3, detection data with the rotation angle detector 8, detection data with the posture detector 9, and the like) in a prototype system will be shown.

Figure 16:
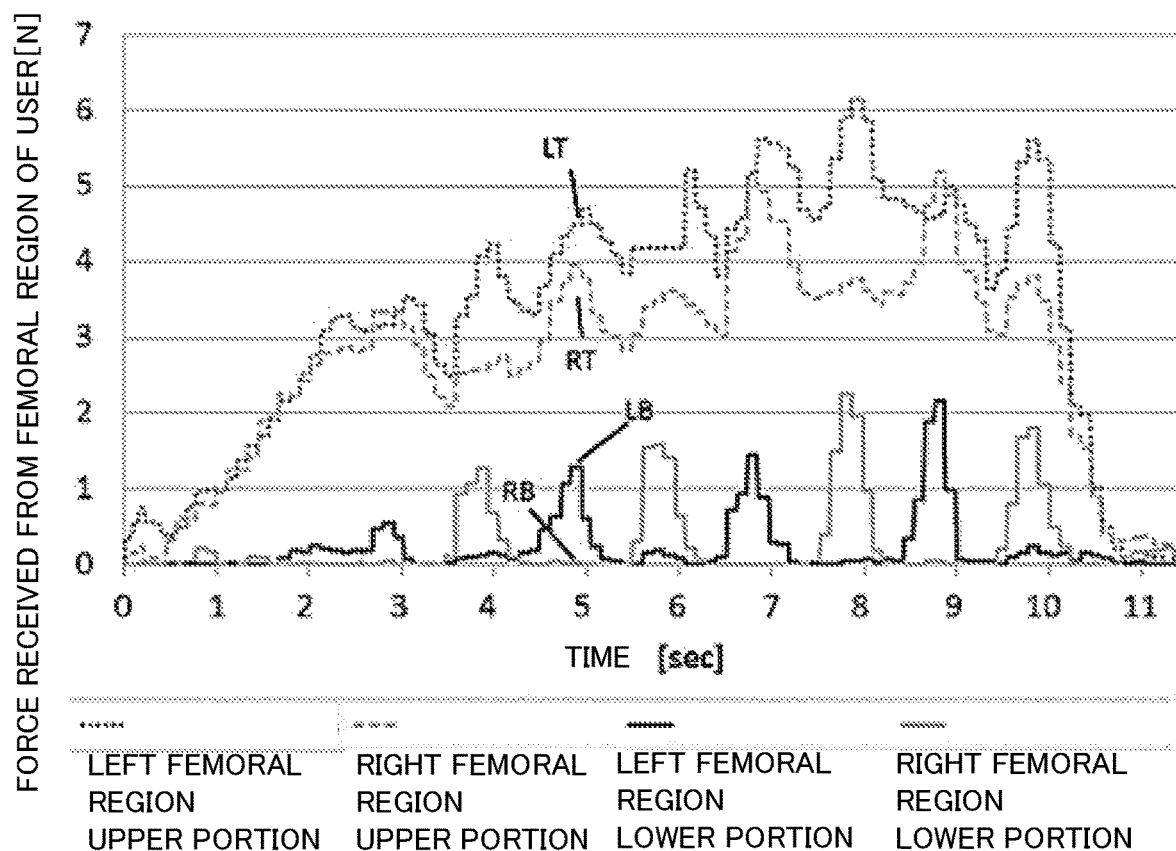
FIG. 16 is a graph of force data received from the femoral region of the user detected by the force detector of the walking sense presentation device according to Embodiment 1 of the present disclosure.

FIG. 16 illustrates an example of variation of detection data of force received from femoral region of the user 1 detected by the force detector 3 of the walking sense presentation device according to Embodiment 1 of the present disclosure. In this graph, the vertical axis represents force received from femoral region of the user 1, and the horizontal axis represents time. In FIG. 16, LT indicates the force received from the left femoral region upper portion of the user 1, LB indicates the left femoral region lower portion, RT indicates the right femoral region upper portion, RB indicates the force received from the right femoral region lower portion, and this makes it possible to estimate the posture of the femoral region of the user 1.

Figure 17:
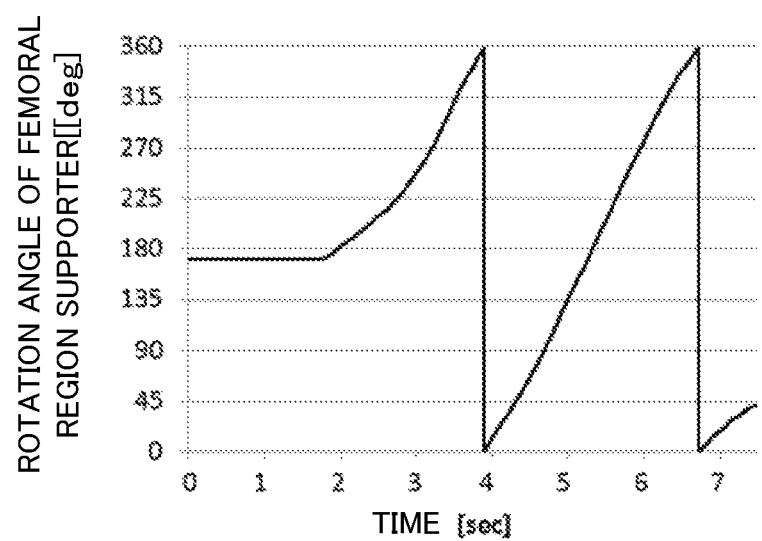
FIG. 17 is a graph of data of a rotation angle of the femoral region supporter detected by a rotation angle detector of the walking sense presentation device according to Embodiment 2 of the present disclosure.

FIG. 17 illustrates an example of data of rotation angles of femoral region supporter 2 detected by the rotation angle detector 8 in the walking sense presentation device according to Embodiment 2 of the present disclosure. In FIG. 17, the vertical axis represents the rotation angles, and the horizontal axis represents the time. With this rotation angle, the waist orientation of the user 1 can be estimated.

Figure 18:
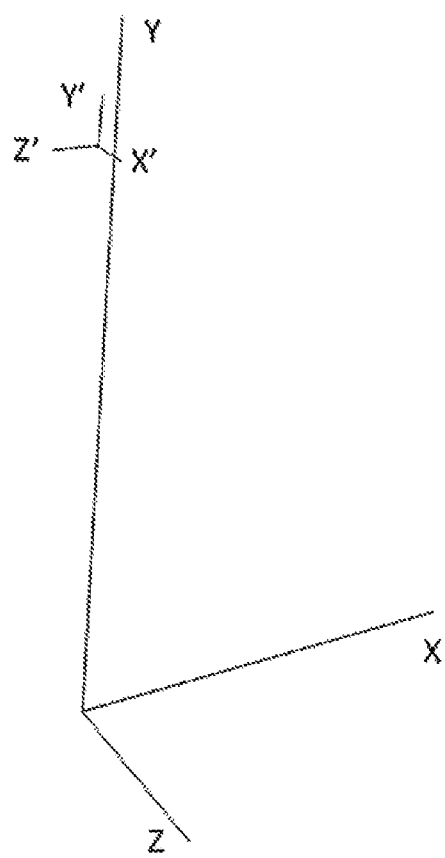
FIG. 18 is a diagram illustrating a coordinate system which defines the posture of the user detected by the posture detector of the walking sense presentation device according to Embodiments 3 and 4 of the present disclosure.

FIG. 18 illustrates a coordinate system that defines the posture of the user 1 detected by the posture detector 9 of the walking sense presentation device according to Embodiments 3 and 4. X, Y, Z of FIG. 18 is an absolute coordinate system with reference to the walking device 10. X', Y', Z' is a coordinate system of the posture of the head of the user 1 estimated by the optical motion capture method. The video generator 5 derives the offset value of the origin and the rotation angle of the X'Y'Z' coordinate system with respect to the XYZ coordinate system based on the posture of the user detected by the posture detector 9, and corrects the video to be displayed.

Figure 19:
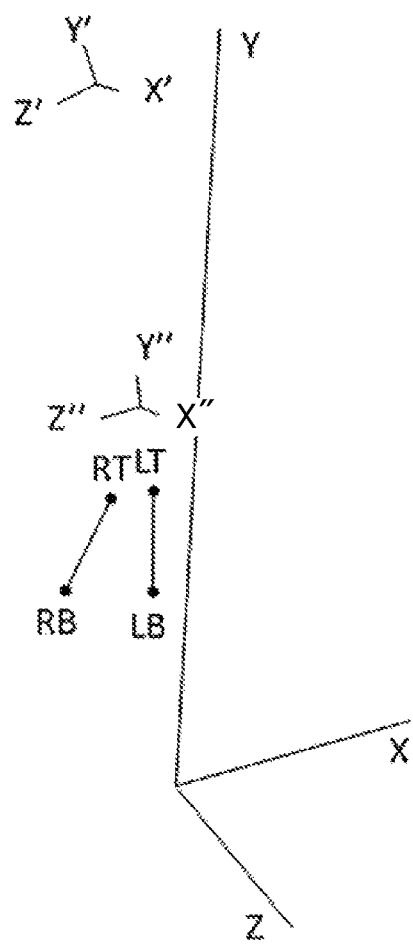
FIG. 19 is a diagram illustrating a coordinate system which defines the posture of the user detected by a force detector, a rotation angle detector, and a posture detector of a walking sense presentation device of the present disclosure.

FIG. 19 illustrates a coordinate system for estimating the walking motion of the user 1 from the data detected by the force detector 3, the rotation angle detector 8, and the posture detector 9 of the walking sense presentation device according to the above embodiment. The coordinate system of X', Y' and Z' in FIG. 19 is a coordinate system indicating the posture of the head of the user 1 estimated by the optical motion capture method. X", Y", Z" is a coordinate system illustrating the posture of the waist of the user 1 estimated from the data detected by the rotation angle detector 8. The walking motion estimator 4 estimates the offset value of the origin and the rotation angle of the X'Y'Z' coordinate system with respect to the XYZ coordinate system. The video generator 5 derives the offset value of the origin and the rotation angle of the X'Y'Z' coordinate system and X"Y"Z" with respect to the XYZ coordinate system, and corrects the video to be displayed based on the offset value and the rotation angle.

In FIG. 19, LT indicates the estimated position of the left femoral region upper portion of the user 1. LB indicates the estimated position of the left femoral region lower portion, RT indicates the estimated position of the right femoral region upper portion, and RB indicates the estimated position of the force received from the right femoral region lower portion. The walking motion estimator 4 estimates the movement amount of the user 1 based on these positions, generates a video according to the movement amount under an appropriate coordinate system, and the video presenter 6 presents the video to user 1. In this way, the user 1 can obtain more realistic walking sense by presenting the video according to the estimated walking motion of the user 1 to the user 1.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-038857, filed on Mar. 2, 2017, the entire disclosure of which is incorporated by reference herein.

INDUSTRIAL APPLICABILITY

The present disclosure can be used, as a device capable of experiencing video and walking sense according to user's walking motion, for game, digital house display, digital fashion, exercise, rehabilitation, appreciation of digital cultural property, online shopping, communication, movement control of robots, and the like.

REFERENCE SIGNS LIST

1 User
1a Estimated walking posture
2 Femoral region supporter
2a Base
2b Support pillar
3 Force detector
3a Femoral region contact portion
3b Force sensor
4 Walking motion estimator
5 Video generator
6 Video presenter
6a Stationary video presentation device
6b Head-mounted video presentation device
7 Rotation mechanism
8 Rotation angle detector
9 Posture detector
10 Walking device
20 Calculator

The invention claimed is:

1. A walking sense presentation device comprising:
a femoral region supporter that supports a femoral region of a user in a direction in which the user travels, the femoral region supporter being fixed to a base on which the user stands and including an upper portion and a lower portion, the femoral region including a femoral region upper portion and a femoral region lower portion;
at least one force detection sensor that detects force received by the femoral region supporter from the femoral region of the user;
a posture detection sensor that detects a posture of the user, is different from the at least one force detection sensor, and is at least one of an angle sensor, an optical camera, or an inertial sensor;
a motion estimator that estimates motion of the user based on the force detected by the at least one force detection sensor and the posture detected by the posture detection sensor;
a video generator that generates video to be presented to the user based on the motion estimated by the motion estimator; and
a video presenter that presents the video generated by the video generator to the user, wherein
at least one of the at least one force detection sensor is provided at the upper portion of the femoral region supporter at which the femoral region upper portion of the user contacts,
at least one of the at least one force detection sensor is provided at the lower portion of the femoral region supporter at which the femoral region lower portion of the user contacts when the user raises the femoral region, and
in a case in which walking motion is about to be performed while the femoral region of the user is supported by the femoral region supporter, the motion estimator estimates, based on force detected by each force detection sensor, a posture of a foot contacting the femoral region supporter.

2. The walking sense presentation device according to claim 1, further comprising:
   a rotation mechanism that rotatably supports the femoral region supporter; and
   a sensor that detects a rotation angle of the femoral region supporter by the rotation mechanism.

3. A walking sense presentation method comprising:
   a first detection step of supporting, by a femoral region supporter, a femoral region of a user in a direction in which the user travels, the femoral region supporter being fixed to a base on which the user stands and including an upper portion and a lower portion, the femoral region including a femoral region upper portion and a femoral region lower portion, and detecting, by at least one force detection sensor, force received by the femoral region supporter from the femoral region of the user;
   a second detection step of detecting, by a posture detection sensor, a posture of the user, the posture detection sensor being different from the at least one force detection sensor and being at least one of an angle sensor, an optical camera, or an inertial sensor;
   an estimation step of estimating, by a calculator, motion of the user based on the force detected in the first detection step by the at least one force detection sensor and the posture detected in the second detection step by the posture detection sensor;
   a video generation step of generating, by the calculator, video to be presented to the user based on the motion estimated and according to change of the posture of the user detected in the second detection step; and
   a video presentation step of presenting the generated video to the user, wherein
   at least one of the at least one force detection sensor is provided at the upper portion of the femoral region supporter at which the femoral region upper portion of the user contacts,
   at least one of the at least one force detection sensor is provided at the lower portion of the femoral region supporter at which the femoral region lower portion of the user contacts when the user raises the femoral region, and
   in a case in which walking motion is about to be performed while the femoral region of the user is supported by the femoral region supporter, the motion estimator estimates, based on force detected by each force detection sensor, a posture of a foot contacting the femoral region supporter.

4. The walking sense presentation method according to claim 3, further comprising:
   a third detection step of allowing the femoral region supporter to be rotatable, and detecting, by a sensor, a rotation angle of the femoral region supporter;
   wherein, in the video generation step, the video to be presented to the user is generated based on the rotation angle in a travel direction of the user detected in the third detection step.

* * * * *